(12) United States Patent
Levin et al.

(10) Patent No.: US 6,241,743 B1
(45) Date of Patent: Jun. 5, 2001

(54) ANASTOMOSIS DEVICE AND METHOD

(75) Inventors: Howard R. Levin, Teaneck, NJ (US); David C. Lundmark, Palo Alto, CA (US)

(73) Assignee: Intellicardia, Inc., New York, NY (US)

( * ) Notice: Subject to any disclaimer, the term of this patent is extended or adjusted under 35 U.S.C. 154(b) by 0 days.

(21) Appl. No.: 09/476,096

(22) Filed: Jan. 3, 2000

Related U.S. Application Data
(60) Provisional application No. 60/134,073, filed on May 13, 1999.

(51) Int. Cl.⁷ .................................................. A61B 17/04
(52) U.S. Cl. .............................................................. 606/153
(58) Field of Search ................................ 606/153, 155, 606/154, 148; 623/1, 11, 12

(56) References Cited

U.S. PATENT DOCUMENTS

| | | | |
|---|---|---|---|
| 4,368,736 | * | 1/1983 | Kaster ................................... 606/155 |
| 4,523,592 | * | 6/1985 | Daniel ................................... 606/155 |
| 4,607,637 | * | 8/1986 | Berggren et al. ..................... 606/155 |
| 5,049,140 | * | 9/1991 | Brenner et al. ...................... 604/266 |
| 5,167,628 | | 12/1992 | Boyles ................................... 604/101 |
| 5,290,227 | | 3/1994 | Pasque ................................... 600/16 |
| 5,308,319 | | 5/1994 | Ide et al. ................................ 600/18 |
| 5,326,374 | | 7/1994 | Ilbawi et al. ............................ 623/3 |
| 5,332,403 | | 7/1994 | Kolff ......................................... 623/3 |
| 5,505,701 | | 4/1996 | Anaya Fernandez de Lomana .. 604/99 |
| 5,755,779 | | 5/1998 | Horiguchi ............................... 623/1 |
| 5,776,190 | | 7/1998 | Jarvik ....................................... 623/3 |
| 5,904,697 | * | 5/1999 | Gifford, III et al. .................. 606/155 |
| 5,922,022 | * | 7/1999 | Nash et al. .............................. 623/1 |
| 6,036,703 | * | 3/2000 | Evans et al. .......................... 606/153 |
| 6,086,527 | | 7/2000 | Talpade ................................... 600/18 |
| 6,117,147 | * | 9/2000 | Simpson et al. ..................... 606/153 |

OTHER PUBLICATIONS

Pawlik et al, Effects of Dimaprit, Prostacyclin, and Acetylcholine on Renal Blood Flow and Function, *Proceedings of the Society for Experimental Biology and Medicine*, 163, 344–349 (1980), pp. 344–349.

* cited by examiner

*Primary Examiner*—Gary Jackson
(74) *Attorney, Agent, or Firm*—Nixon & Vanderhye P.C.

(57) ABSTRACT

This is an implantable device intended generally for forming an anastomosis between a lumen of the body and an intersecting graft lumen. The device may be configured to form an anastomosis which is entirely lined with live tissue, or it may be configured to form an anastomosis with synthetic material defining at least a portion of one of the intersecting lumens.

20 Claims, 8 Drawing Sheets

ANASTOMOSIS DEVICE AND METHOD

This application claims benefit to U.S. provisional application serial No. 60/134,073 filed May 13, 1999.

TECHNICAL FIELD

The present invention relates to surgical devices for anastomosis procedures requiring the union of luminal structures of the body, such as blood vessels or bile ducts, and more particularly, relates to coupling devices which eliminate the use of traditional suturing techniques for coupling such vessels in surgical procedures.

BACKGROUND ART

Among the important and time consuming tasks in surgical procedures is the anastomosis or joining of severed blood vessels, and the success of a surgical procedure may depend on the degree of circulation which is restored through such anastomosis. Anastomosing of blood vessels is a tedious procedure, particularly in blood vessels of small diameter including blood vessels less than one mm. in diameter. Conventional blood vessel suturing techniques are time consuming, extending the duration of a surgical procedure and successful anastomosing of blood vessels is highly dependent on the proper placement of sutures by the surgeon. Similar difficulty is often encountered in anastomosing synthetic tubular graft materials to existing vessels of the body.

Various methods and devices for performing an end-to-side anastomosis are known within the art of surgery. Most of these known methods are, however, time-consuming, and thus not suitable for use when time is at a premium and a quiet field of operation is needed, as for example in the case of coronary bypass operations.

U.S. Pat. No. 4,624,255 discloses an anastomosis device wherein a member, preferably in the form of a ring, has structure for tethering the blood vessel portions thereto under radial stress with the intima of the blood vessel portions opposed. During surgery, the ring is disposed around an end of one of the severed blood vessel portions, and the blood vessel portions are tethered to the ring at least three spaced apart locations stressing the blood vessel portions radially outward in several directions to evert the intima and hold the intima of the two portions against each other. To hold blood vessel portions in close proximity during anastomosis, a pneumatic clamping device is provided which grips the blood vessel portions with a force according to the fluid pressure supplied thereto.

U.S. Pat. No. 4,523,592 discloses an anastomotic coupling device wherein a pair of coupling disc members cooperate to couple two vessels, one of the members having spaced apart hook members, and the other member having receptor cavities aligned with said hook members for locking the members together in a successful anastomatic procedure with tissue everted and secure on said hook members.

U.S. Pat. No. 4,366,819 discloses an anastomotic fitting for coronary artery bypass graft surgery having an assembly of four components including a cylindrical tube having at least one ring flange locking indentation in an inflow end and a plurality of locking ring grooves in an outflow end, a ring flange having a central aperture and pluralities of long and short spikes, the long spikes engaging in the locking indentation, with a graft engaged therebetween, a fixation ring having a central aperture and a plurality of spikes positioned about the aperture, and a locking ring having an aperture with a plurality of locking ring ridges for engagement with the locking ring grooves. At surgical implantation an aortic wall having a hole therein engages between the ring flange and the fixation ring and is held in position by the spikes of the fixation ring, and the four components engage together forming an integral anastomotic fitting.

U.S. Pat. No. 5,366,462 discloses a method of using a staple for joining first and second blood vessels wherein a staple having an open center is provided to staple the two vessels together. One end of the first blood vessel is placed through the staple and then pierced by an end of the staple. An opening in the side of the second blood vessel is formed and the pierced end of the first blood vessel is inserted into the hole. A second end of the staple is then deflectively bent and pierces the outer wall of the second vessel to staple the two vessels together.

U.S. Pat. No. 4,917,087 discloses devices, kits and methods for non-suture end-to-end and end-to-side anastomosis of tubular tissue members employing tubular connection members having clip retaining elements comprising annular groove or flanges in the connection members and spring clips which comprise a ring-shaped body with separable opposed ends whereby a circular opening defined by the body can be enlarged. The opposed ends have handling elements to facilitate handling of the clips and separation of the opposed ends.

It is a general object of the present invention to provide methods and apparatus which simplify surgical anastomosis techniques and which effect an anastomosis with substantial assurance of patency.

SUMMARY OF THE INVENTION

This invention is an device and method for creating an anastomosis between a body lumen and a intersecting graft lumen. Each embodiment requires the action of extension members which may be placed through a relatively-small hole and expanded in size to facilitate formation of the anastomosis.

One variation of the inventive device includes an implantable structural member having proximal and distal structural member ends, a longitudinal axis, an outer structural member surface, a structural member inner lumen, and at least two extensions extending outward from the structural member surface at the distal structural member end. The implantable structural member is attachably interfaced with an implantable fastener having proximal and distal fastener ends and an inner fastener surface. The inner fastener surface has a configuration wherein it will attachably interface with the outer structural member surface. The proximal end of the implantable structural member, in turn, is configured to attach to and become partially encapsulated by the tubular graft. The at least two extensions are configured to bend against the structural member surface when the implantable structural member is urged, distal structural member end first, through a small diameter hole in the tissue wall and to bend outwardly from the structural member surface to prevent the implantable structural member from being removed from the small diameter hole when the implantable structural member is moved in a reverse direction. The implantable fastener is configured to lock the implantable structural member into a final implanted configuration so that the tissue wall is compressed between the distal end of the implantable fastener and the at least two extensions.

The invention includes a method for using such a device to form an anastomosis.

In another variation of the inventive device, an insertion structure having a main shaft, proximal and distal ends, and at least two radial extensions, the at least two radial extensions being coupled to the tubular graft and releasably coupled to the main shaft, is configured to be coupled with a threadlike wall attachment member in a configuration wherein the at least two radial extensions are configured to bend toward the main shaft when a deployment construct, comprising the insertion structure with the main shaft partially encapsulated by the tubular graft and the tubular graft releasably attached to the expandable implant, is urged, main shaft distal end first, through a small diameter hole in the tissue wall from the external to the interior side, and to bend outwardly from the main shaft to prevent the deployment construct from being removed from the small diameter hole when main shaft is urged in a reverse direction, and wherein the threadlike wail attachment member is attachable to the at least two radial extensions from the external side of the tissue wall, the threadlike wall attachment member operating to urge the radial extensions toward the lumen side of the tissue wall, thus placing the tissue wall and the tubular graft in compression against each other.

DETAILED DESCRIPTION OF THE INVENTION

This invention is a device and method for efficiently creating an end-to-side anastomosis between the end of a tubular member and a tissue wall of another member. The inventive device has two primary variations: a synthetic-lumen variation and a live-lumen variation. Each of these primary variations is based upon the same principles, but uses different materials to accomplish the goal of fluidly connecting the end of a tubular member with the wall of another member. More specifically, the synthetic-lumen variation provides an anastomosis wherein fluids passing between the tubular member and the confines of the associated tissue wall through the anastomosis junction encounter a lumen portion which is primarily defined by an exposed layer of synthetic material such as a polymer. In contrast, the live-lumen variation provides an anastomosis wherein fluids passing between the lumen defined by the tubular member and the confines of the associated tissue wall interface with lumen-defining walls primarily comprised of live tissue. An important common aspect of each variation is the use of radially disposed extensions configured to collapse to a relatively small diameter during a "push in" step of implantation and expand to a relatively large diameter during a "pull out" step of implantation, operating somewhat like the action of the structure which supports the fabric of an umbrella.

Figure 1:
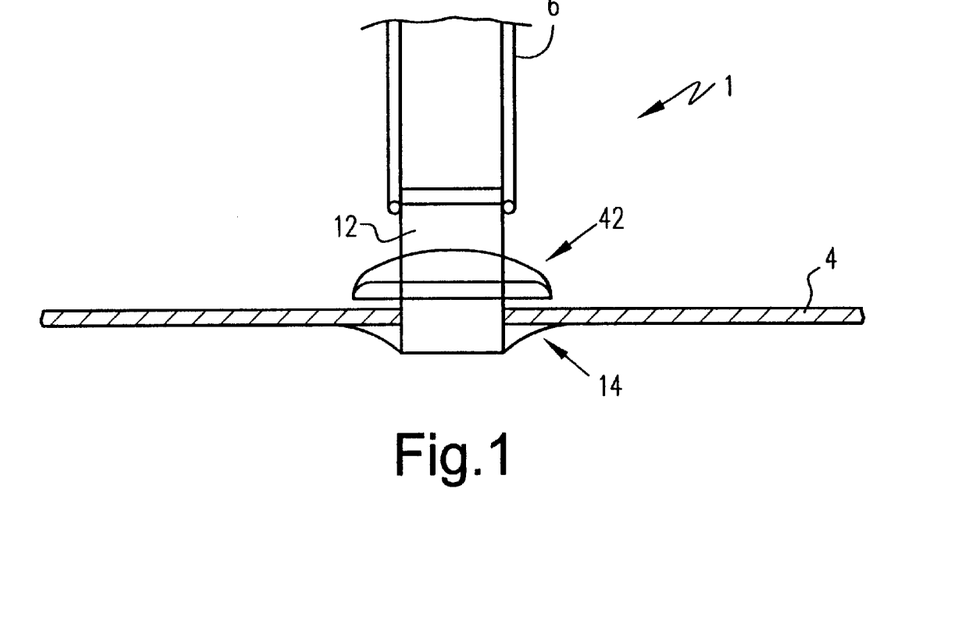
FIG. 1 depicts a side view of a synthetic-lumen variation of the inventive device.
Figure 2:
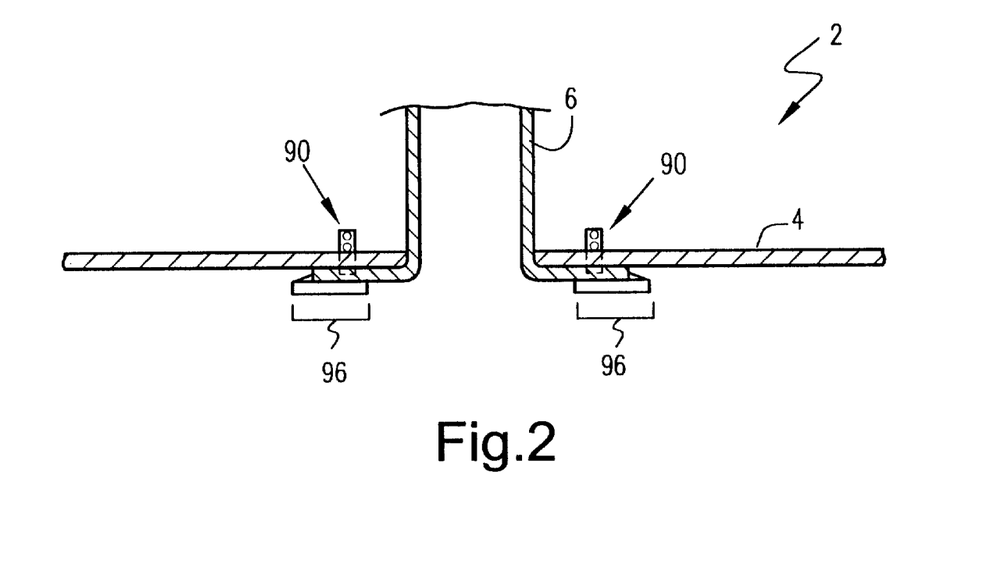
FIG. 2 depicts a sectional side view of a live-lumen variation of the inventive device.

Referring to FIGS. 1 and 2, side views of synthetic-lumen (1) and live-lumen (2) anastomosis devices in final implantation configurations are depicted. In FIG. 1, an end portion of a tubular graft (6) is shown coupled approximately perpendicularly to a tissue wall (4) using a fastener (42) and a synthetic structural member (12) having radial extensions (14) to urge a portion of the tissue wall (4) into compression between the fastener (42) and the radial extensions (14), thus providing fixation for the synthetic structural member (12) and associated tubular graft (6).

In FIG. 2, an end portion of a tubular graft (6), in this variation a live tissue graft preferably comprised of human endothelial tissue, is shown coupled to a tissue wall (4) using detached insertion structure radial extension portions (96) which are coupled to a circumferential exterior retention saddle (90) in a manner wherein the tubular graft (6) and tissue wall (4) are fixated in compression against each other.

Figure 3A:
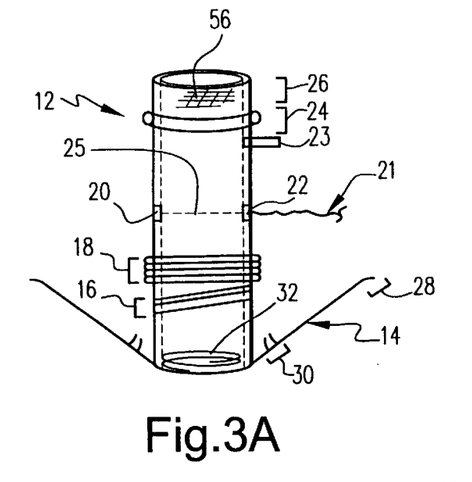
FIG. 3A depicts a side view of a structural member of a synthetic-lumen variation of the inventive device.
Figure 3B:
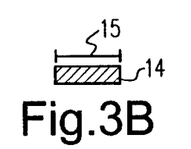
FIG. 3B depicts a cross sectional view of a variation of a radial extension of a synthetic-lumen variation of the inventive device.

FIGS. 3A and 3B depict variations of the synthetic structural member (12) in greater detail. Referring to FIG. 3A, a side view of a structural member (12) is shown. The structural member (12) is generally tubular, defining a structural member inner lumen (56) and having an outer surface which is configured to form a threaded (16) or groove-locking (18) interface with the inner surface of a fitted fastener. Groove-locking interfaces are well known in the art of small, particular polymeric, fittings and are described in publications such as U.S. Pat. No. 4,366,819 for similar uses. Groove-locking interfaces generally comprise two matched surfaces having parallel undulations formed therein, the surfaces being forced against each other, say in an interference fit between a ring and a shaft, wherein the surfaces may be moved in relation to each other against the interference fit of the grooves after a threshold shear force has been developed between the surfaces against the longitudinal direction of the grooves in each surface, and wherein the surfaces will remain interlocked if forces less than the requisite threshold shear force are developed.

As shown in the drawing, a sew ring (24) may be coupled to the outer surface of the structural member (12) to facilitate attachment of a tubular graft member. The compliant sew ring (24), preferably comprised of a compliant yet fracture-tough composite material made from a polymeric foam reinforced by small diameter polymeric fibers, is coupled to the structural member (12) using adhesives or partial encapsulation as in the preferred embodiment.

The structural member is preferably comprised of a synthetic material, such as a polymer, which is biocompatible, may be precisely formed and machined, and has a stiffness high enough to prevent kinking and significant deformation under loads resulting from installation and implantation. Most preferred is ultra-high molecular weight polyethylene (UHMWPE). As shown in FIG. 3A, the walls of the structural member (12) may be fitted with sensors or sensor portions (20, 22) for monitoring parameters of adjacent tissues, such as temperature, oxygen level, hematocrit level, or flow rate. Such sensors or sensor portions may be coupled to the structural member using adhesives, interference fit, encapsulation, combinations of these, or other standard methods. Certain sensors, such as blood oxygen monitoring sensors, may emit and detect light within the lumen (56) to operate, and therefore may require direct access to the lumen, or have only a lucent layer of material between themselves and the tissues flowing within the lumen (56). Such sensors may have conductive leads (21) which are configured to transmit energy or signal information to and/or from other devices. Suitable sensors, including oxygen sensors such as those comprising a light emitting device, pressure sensors such as those comprising a piezoelectric transducer or a crystalline silicon chip, fluid flow sensors such as those based upon Doppler transducer theory, hematocrit sensors, temperature sensors, heart electrical signal sensors, biochemical sensors, pH level sensors, and blood electrolyte sensors are further discussed in U.S. Patent application for "Instrumented Stent", attorney docket number 3659-6, which is incorporated by reference in its entirety.

Internal leads (25) which electrically connect one portion of a sensor (20) to another (22), as in the case of a light emitting portion and a light detecting portion, may be encapsulated within the material comprising the structural member (12). The structural member may also define a side input lumen (23), preferably configured to facilitate fluid couplement between the structural member lumen (56) and a medicine reservoir of a medicine pump (not shown), which may be implantable. Suitable medicine pumps are known in the art and are described in references such as U.S. Pat. Nos. 5,820,589, 5,207,666, and 5,061,242.

The variation depicted in FIG. 3A may be coupled with the tubular end of a synthetic or live graft. In the case of a live graft, it may be desirable to have a porous region (26) at the end of the structural member (12) through which a live graft could obtain flow-based nutrition. In other words, live graft material such as vein autograft or artery autograft is made tip of endothelial tissue which receives necessary nutrition from surrounding fluids; having a porous substrate material through which the endothelial tissue could receive blood-based nutrients is preferred because it may enhance the probability of live tissue sustenance. The pores of the porous region (26) extend through the wall of the structural member (12) around a particular circumferential surface of the structural member (12), as shown in the figure; they do not form a filter through which flows in the structural member (12) lumen must pass.

Also shown in FIG. 3A are radial extensions (14), coupled to the structural member (12) and configured to expand outwardly when not loaded, as shown, to bend toward the structural member (12) when loaded by forces resulting during a "push in" step of installation as described below, and to bend outwardly to a maximum bending position which is nearly perpendicular to the structural member during a "pull out" step of installation, as described below. The radial extensions (14), generally comprised of a flexible metal such as titanium or nickel-titanium alloy, may be coupled to the structural member (12) using adhesives, an interference fit wherein a portion of the radial extension forms a ring around the structural member, partial encapsulation, or other standard manufacturing techniques. Preferably, spiralled portions (32) of the radial extensions (14) are partially encapsulated by the material which forms the structural member (12), as is shown in the drawing. The encapsulated spiralling (32) results in a desirable stiffening of the end of the preferably polymeric structural member (12) and an interface between structural member (12) and radial extension (14) which facilitates cantilevered bending of the radial extensions (14) during installation and implantation of the device, as described below. Also shown coupled to the depicted variation of the radial extensions are extension pins (30), preferably comprised of the same material as their radial extension substrate and coupled thereto with welds, adhesive, or other standard techniques, or formed from the same piece of material as the radial extension (14) and plastically deformed upward, as in the depicted variation.

Figure 3C:
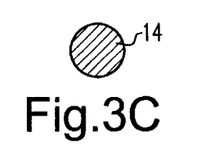
FIG. 3C depicts a cross sectional view of a variation of a radial extension of a synthetic-lumen variation of the inventive device.

Referring to FIGS. 3B and 3C, cross sectional side views of two variations of a radial extension (14) are shown to illustrate potential cross sectional geometries. FIG. 3B depicts a variation of a radial extension (14) having a rectangular cross sectional geometry. Due to its large tissue contact side surface area (15), this geometry is preferred with relatively elastic tissue walls, which are able to stretch and accommodate a relatively large-diameter folded implant without need for a large-diameter implantation aperture. FIG. 3C depicts another variation of a radial extension (14) having a roughly circular cross sectional geometry. This radial extension shape is preferred with relatively inelastic tissue walls because many circular cross section radial extensions, preferably more than six, may be closely urged against the structural member (12) during implantation so a smaller installation aperture is needed and tighter overall fit may result while still facilitating a strong fixation due to the multitude of radial extensions (14) available to place the tissue wall in compression between a fastener (42) and the radial extensions (14).

Figure 3D:
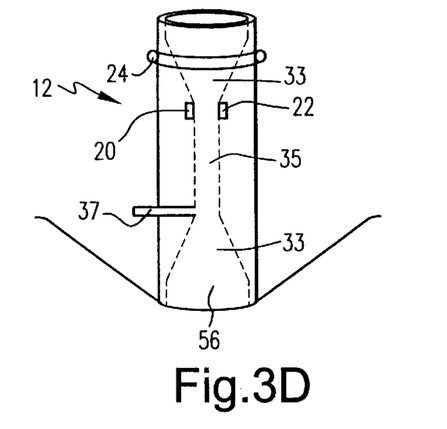
FIG. 3D depicts a side view of a structural member of a synthetic-lumen variation of the inventive device.

Referring to FIG. 3D, another variation of the inventive structural member (12) is depicted having a structural member lumen (58) geometrically configured to have an internal venturi shape comprised two conical tapered regions (33) a venturi throat (35) and a venturi input lumen (37) a the region of low pressure created when fluids are forced through the venturi throat at high velocities. The phenomena of high velocity and related low pressure using similar geometries is well known in the art of fluid mechanics, and is described in publications such as *Fluid Mechanics, Second Edition*, by Frank M. White, McGraw Hill, 1986. Also shown in the depicted variation are sensors or sensor portions (20, 22) configured to measure parameters of fluids flowing within the structural member lumen (58). The dimensions of the venturi throat are preferably configured for the particular patients or groups of patients, based upon the pressures available in the vessel lumen and the viscosity of the blood of the individual. As relatively high pressure is required upstream of the structural member (12) to create significant flows in the venture input lumen (37), the venturi variation may not be appropriate for all patients, especially those at risk for vessel aneurysm. For such patients, the input of fluids such as medicine or blood is preferably augmented by a fluid pump.

Figures 4, 5:
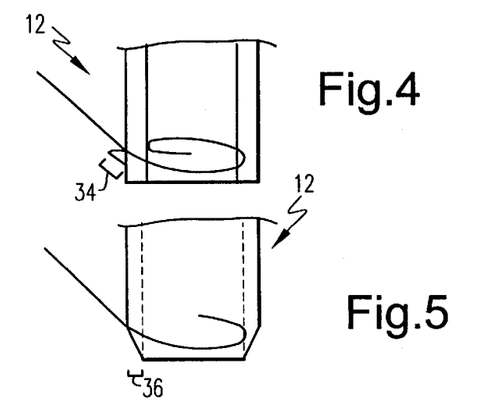
FIG. 4 depicts a partial side view of a structural member of a synthetic-lumen variation of the inventive device.
FIG. 5 depicts a partial side view of a structural member of a synthetic-lumen variation of the inventive device.

Referring to FIG. 4, a partial cutaway side view of a variation of the inventive structural member (12) is shown having a cantilever support portion (34) which extends outward and is configured to support the radial extension (14) as it is placed in cantilever bending during installation and implantation, as described below. A cantilever support portion is particularly useful to prevent bucking of radial extension members (14) comprised of relatively stiff materials, and to prevent over-bending (past the desired maximum downward bending position which is approximately parallel to the tissue wall against which the radial extension (14) is urged during installation and implantation) of radial extension members comprised of particularly flexible materials such as some nickel-titanium alloys.

Referring to FIG. 5, a partial sectional side view of a variation of the inventive structural member (12) is shown having a tapered end region (36) which is configured to slide more easily through a relatively small-diameter aperture created in a tissue wall upon implantation, as described below. The angle of tapering of the tapered end region (36) is generally configured to match that of a trocar, depicted in FIG. 8 and described below, which may be used to create a small aperture in the tissue wall (4) through which a portion of the device is passed during implantation.

Figure 6:
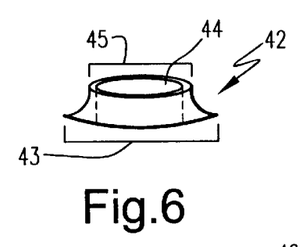
FIG. 6 depicts an orthogonal view of an implantable fastener of a synthetic-lumen variation of the inventive device.

FIG. 6 shows an orthogonal view of a variation of the fastener (42) designed to interface with the outer surface of the structural member (12) and hold the tissue wall (4) in compression after installation. The fastener is preferably comprised of similar materials as the structural member (12), ultra-high molecular weight polyethylene being most preferred. The fastener (42) has an inner lumen (44) configured to interface with the outer surface of the structural member. More particularly, the fastener is configured to slide along the outer surface of the structural member (12) with relative freedom, and to interface using threads (16) or undulations(18) (for a groove-locking interface) with the portion of the structural member (12) outer surface configured with like geometric features. As shown in FIG. 6, the outer surface geometry of the fastener (42) is configured to be easily manipulated, or more particularly pressed downward, by the fingers of a person conducting an installation. The bottom cross sectional area (43) of the fastener (42) is large relative to the top cross sectional area (45) to spread compressive loads generated at the interface between the fastener (42) and the tissue wall (4) over a larger surface area, as well as for ergonomic reasons.

Figure 7:
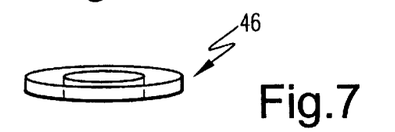
FIG. 7 depicts an orthogonal view of a compliant washer member of a synthetic-lumen variation of the inventive device.

Referring to FIG. 7, a compliant load ring (46) is shown in orthogonal view. The compliant load ring (46) has an inner diameter configured to slidably interface with the outer surface of the structural member (12) and an outer diameter approximately equal to that of the fastener (42). The compliant load ring (46), preferably comprised of a relatively compliant biocompatible material such as polyurethane or cotton felt, is designed to prevent localized compressive stress concentrations which may occur between the bottom surface of the fastener (43) and the associated tissue wall (4) during installation and implantation.

Figure 8:
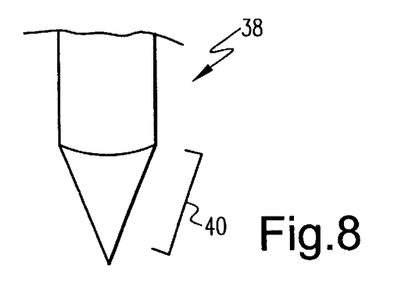
FIG. 8 depicts a side view of a trocar designed for use with a synthetic-lumen variation of the inventive device.

FIG. 8 depicts a trocar (38) having a tapered distal end (40) which is suitable for assisting in the installation of the inventive device. The outer diameter of the trocar (38) is slightly smaller than the structural member (12) inner lumen (56) diameter so the trocar (38) may be slidably positioned within the lumen (56) and then slidably removed after an aperture has been created in the tissue wall (4) using the tapered distal end (40) of the trocar (38).

Figure 9A:
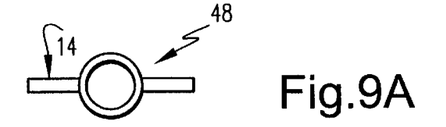
FIGS. 9A–9C depict partial bottom views of different variations of a structural member of a synthetic-lumen variation of the inventive device.
Figure 9B:
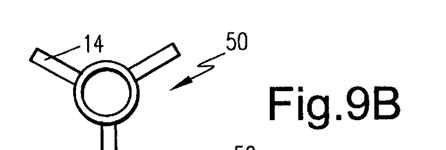
Figure 9C:
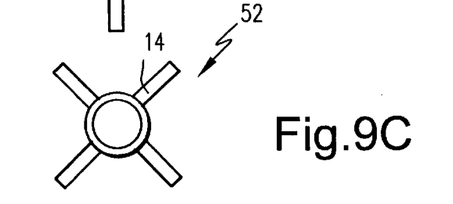

Referring to FIGS. 9A–9C, partial bottom views of different variations of a synthetic structural members (12) with radial extensions (14) of a synthetic-lumen variation of the inventive device are shown. FIG. 9A shows a variation having two radial extensions (14). FIG. 9B shows a variation having three radial extensions (14). FIG. 9C shows a variation having two radial extensions (14). The number of radial extensions (14) required for adequate device fixation depends upon the compliance of the tissue wall (4) and the stress concentration which the tissue wall (4) can withstand without being physiologically compromised. A variation having at least three radial extensions (14) is preferred in scenarios wherein the tissue wall comprises human endothelial tissue such as healthy venous or arterial tissue of a large vessel.

Figure 10A:
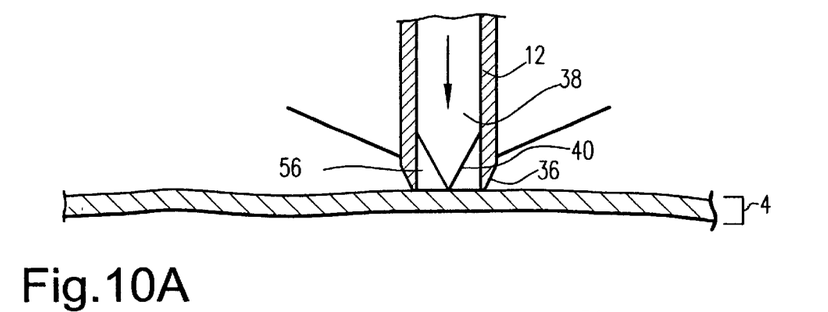
FIGS. 10A–10E depict a method for installing a synthetic-lumen variation of the inventive device.
Figure 10B:
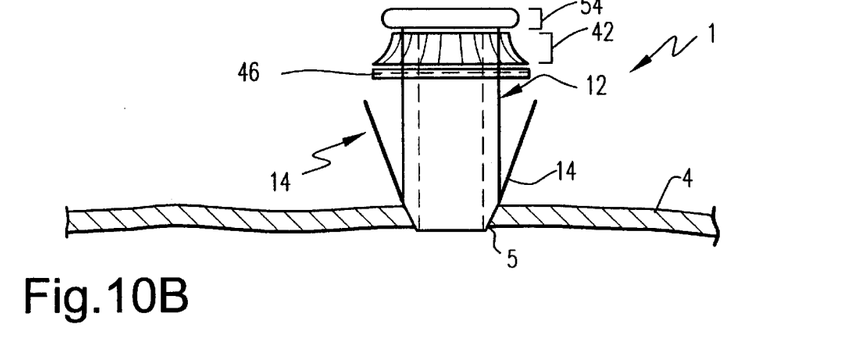

FIGS. 10A–10E depict a method for installing a synthetic-lumen variation of the inventive device. As shown in FIG. 10A, the structural member (12) is placed in contact with the tissue wall (4) to be anastomosed. A trocar (38) is slidably mounted within the structural member (12) lumen (56) having a tapered end (40) matched to the tapered end portion (36) of the structural member (12). FIG. 10B shows a device (1) partially inserted into a tissue wall (4) aperture (5). The trocar has been slidably removed and a removable cap (54) placed upon the structural member (12) to prevent fluids from flowing up and out of the structural member lumen (56). The removable cap (54) is preferably comprised of an easily formable and machinable polymer material with enough stiffness to snap into place in a slight interference fit, such as ultra-high molecular weight polyethylene, polyethylene, polypropylene, polybutylene, and mixtures and copolymers thereof. The drawing shows the radial extensions (14) being bent upward as the device is pushed through the aperture (5) in the tissue wall (4). Also shown are a fastener (42) and a compliant load ring (46) slidably interfaced with the top portion of the structural member (12).

Figure 10C:
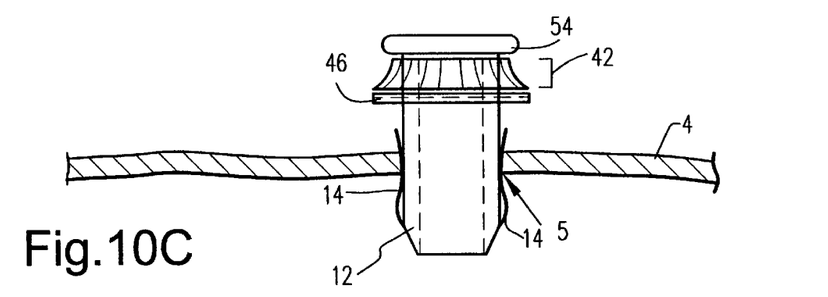

Referring to FIG. 10C, the device construct shown in FIG. 10B has been advanced further downward into the confines of the tissue wall (4). As shown in the drawing, the radial extensions (14) are bent into a configuration wherein they are pressed nearly flush against the structural member (12) as the device is pressed, or "pushed in", through the aperture (5) in the tissue wall (4).

Figure 10D:
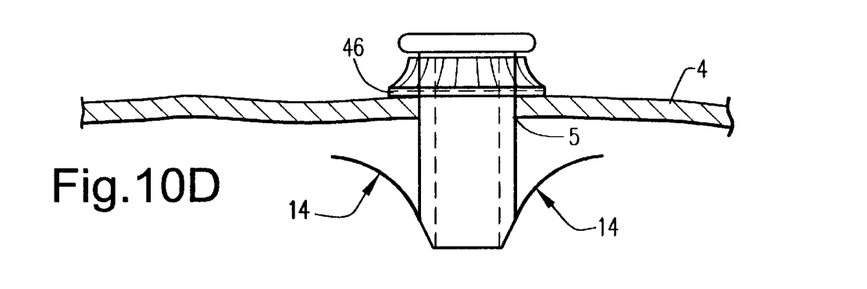

FIG. 10D shows the device advanced to a depth within the confines of the tissue wall (4) at which the radial extensions (14) are able to spring back to their unloaded position, as shown in the drawing. In this configuration, the device has been pushed in as far as is necessary for proper installation.

Figure 10E:
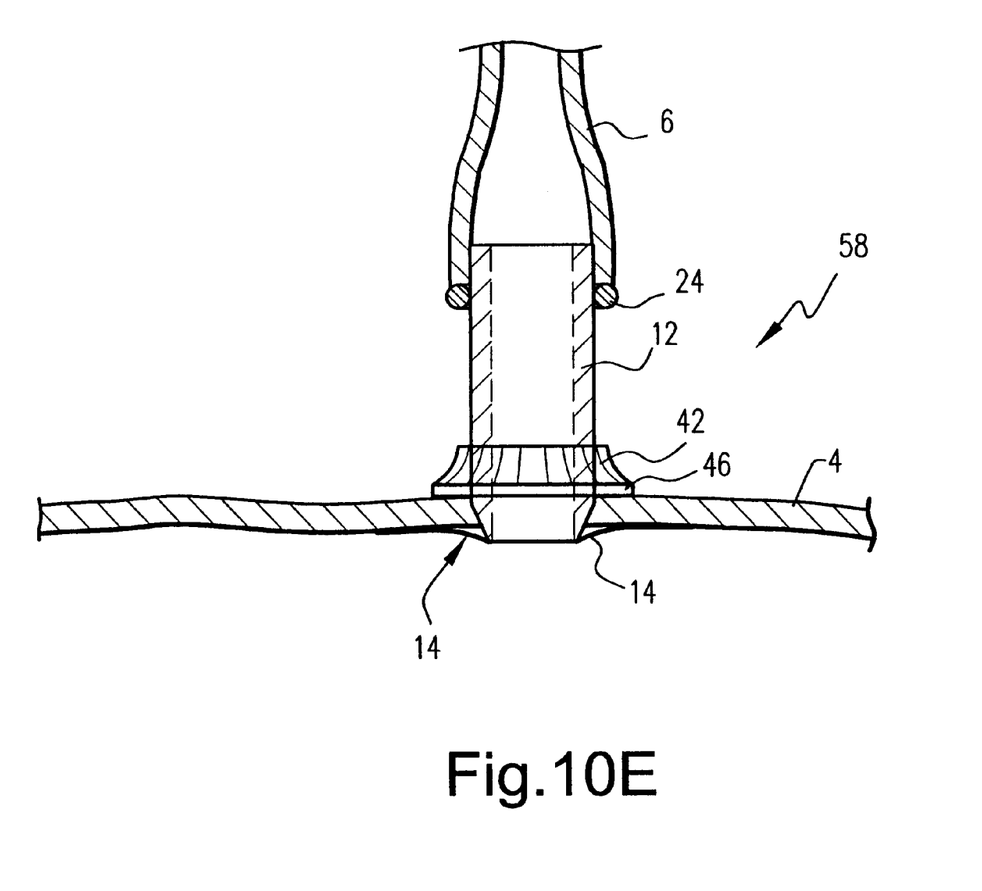

FIG. 10E depicts the device after the structural member (12) has been pulled in a reverse direction, or "pulled out", into a configuration as shown wherein the radial extensions (14) are urged against the tissue wall (4) and forced into cantilever bending. The position is retained after the fastener (42), shown in side view, has been pushed down and locked into place against the compliant load ring (46) using threads or groove-locking, thus placing the tissue wall (4) into compression between the compliant load ring (46) and the radial extensions (14). Also shown in the figure is a graft member (6) coupled to the structural member (12) after removal of the removable cap (54), in this example via stitches through a sew ring (24) attached to the top of the structural member (12).

Referring to FIGS. 11A–11I, various partial side views and partial orthogonal views of a live-lumen variation of the inventive device are depicted.

Figure 11A:
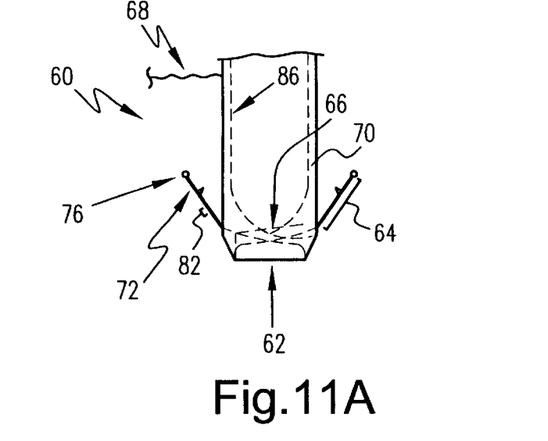
FIG. 11A depicts a side view of an insertion structure of a live-lumen variation of the inventive device.

FIG. 11A depicts a partial side view of a live-lumen insertion structure (60). As shown in the figure, an insertion structure main shaft (70) is coupled to at least two radial extensions (64). The ends of the radial extensions (64) are configured to attach to the ends of a live tubular graft member.

In the depicted embodiment, the ends of the radial extensions (64) comprise radial extension graft connection portions (76) configured to facilitate coupling between a graft and radial extensions (64) using a suture (not shown). The radial extensions (64) are preferably comprised of a flexible material, such as a nickel-titanium alloy, which is capable of withstanding significant bending without structural failure or plastic deformation. To facilitate cantilevered load bearing by the radial extensions (64) they are fixedly coupled to the main shaft (70) of the insertion structure (60) using adhesives, encapsulation, or other known techniques. In the depicted variation, the ends of the radial extensions (64) are encapsulated by the material forming the main shaft (70) in a spiral fashion (66); the spiralling is better shown in FIG. 3A for another variation of the inventive device. The radial extensions (64) may have shapes and configurations similar to those shown for the synthetic-lumen variation of the inventive device in FIGS. 9A–9C and 3C–3D.

The main shaft of this variation is designed to be detachable from the ends of the radial extensions because leaving it in place after the anastomosis is formed would be leaving a large mass at the middle of the flow path for blood moving through the anastomosis—a potential thrombogeneity risk problem. In other words, a clot could form at upon the mass due to the concentrated flow, and could later be thrown off into the circulatory system. Therefore it is desirable to leave a clear flow path within the anastomosis, and thus the main shaft is removable. FIG. 11A depicts both a release lead (68) and a pull wire (86). The release lead (68) is depicted to demonstrate that the main shaft (70) or a portion thereof may be configured to conduct electricity between a power source (not shown) and an electrolytic detachment zone (82) designed to erode upon application of electric current. The pull wire (86) is depicted to illustrate that portions of the radial extensions (64) may be mechanically detachable through actuation of a pull wire (86) which uncouples a detachable portion when pulled outward, the pull wire (86) being configured to have an arcuate path through the main shaft (70) of the insertion structure (60) to minimize friction between the materials comprising the main shaft (70) and the pull wire (86).

Also depicted in the variation of FIG. 11A is a insertion structure lumen (62) configured to facilitate use of a trocar (not shown) which may slidably engage the walls of the insertion structure (60) defining the lumen (62). Many suitable trocars with approximately cylindrical cross sectional geometries and pointed tips are known in the art. The figure also illustrates that sew posts (72) are coupled to the radial extensions (64) and configured to push through the tissue wall into which they are forced during installation of the device.

Figure 11B:
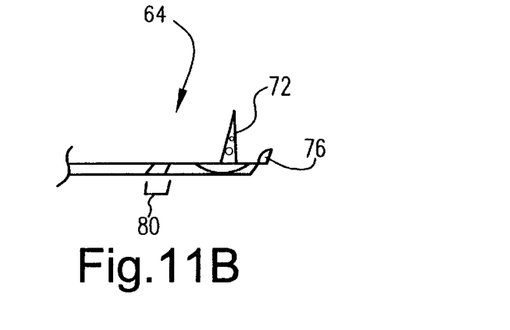
FIG. 11B depicts a partial side view of an insertion structure of a live-lumen variation of the inventive device.
Figure 11C:
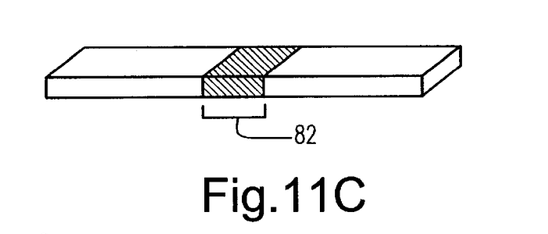
FIG. 11C depicts a partial side view of an insertion structure of a live-lumen variation of the inventive device.
Figure 11D:
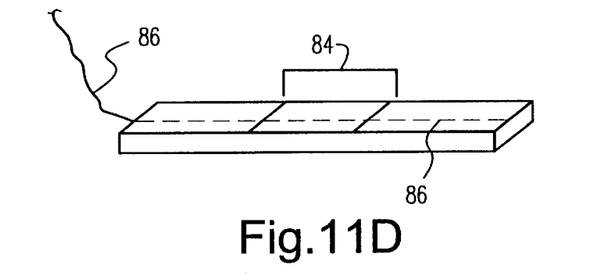
FIG. 11D depicts a partial side view of an insertion structure of a live-lumen variation of the inventive device.
Figure 11E:
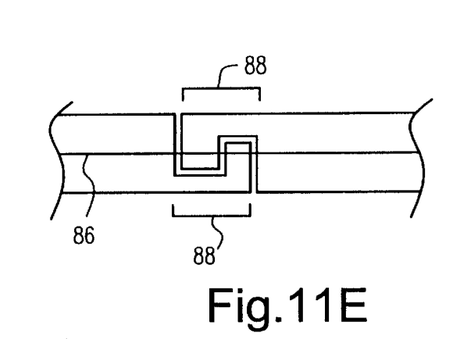
FIG. 11E depicts a partial side view of an insertion structure of a live-lumen variation of the inventive device.

Referring to FIG. 11B, a close-up side view of a variation of a radial extension (64) is shown having a sharpened sew post (72) and a small eyelet as a graft connection portion (76), the small eyelets being configured to accept a suture configured to couple a graft end to the radial extensions (64). The sharpened sew posts (72) are termed "sew posts" because they are configured to accept a suture. This figure, as well as FIGS. 11C, 11D, and 11E, each a close up side view of a radial extension (64) variation, illustrate that the radial extension (64) has a dislocation region (80) which may comprise an erodable link (82) or a mechanically detachable link (84).

Suitable erodable links are disclosed in references such as U.S. Pat. Nos. 5,354,295, 5,122,136, 5,891,128, 5,423,829, and 5,624,449. Suitable mechanically-detachable links are disclosed in references such as U.S. Pat. Nos. 5,304,195 and 5,250,071.

Figure 11F:
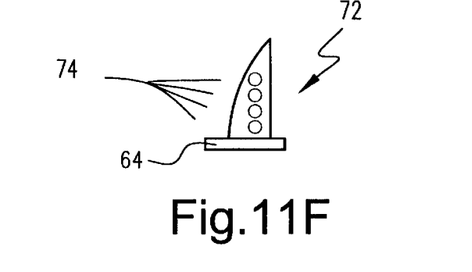
FIG. 11F depicts a partial side view of an insertion structure of a live-lumen variation of the inventive device.
Figure 11G:
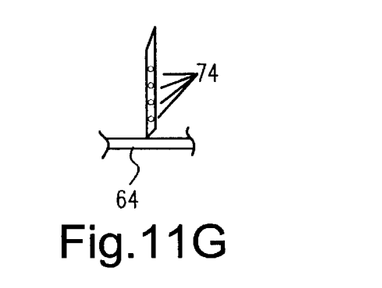
FIG. 11G depicts a partial side view of an insertion structure of a live-lumen variation of the inventive device.

Referring to FIGS. 11F and 11G, close-up end and side views, respectively, are shown of a variation of the inventive radial extension (64) specifically showing details of a sew post (72) variation. The sew post (72) preferably has a sharpened tip and a multitude of apertures (74) configured to accommodate sutures therethrough during installation of the device. The sew posts (72) of this variation are welded in place upon the substrate metal material which forms this variation of radial extensions (64).

Figure 11H:
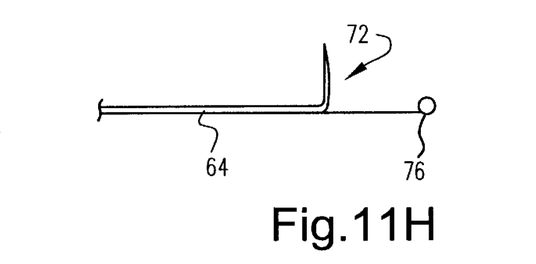
FIG. 11H depicts a partial side view of an insertion structure of a live-lumen variation of the inventive device.
Figure 11I:
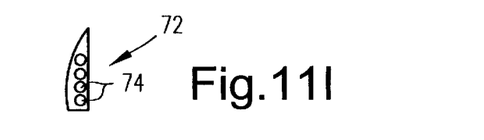
FIG. 11I depicts a partial side view of an insertion structure of a live-lumen variation of the inventive device.

Referring to FIGS. 11H and 11I, close-up side and end views, respectively, of a variation of the inventive radial extension (64) are shown. These figures depict a similar sew post (72) geometry as that of the previous figures, with the exception that the sew posts (72) depicted in FIGS. 11H and 11I are formed from the same piece of material which comprises the substrate radial extensions (64). Preferably they are bent up into position like splinters or wedges of the material after apertures (74) have been formed in the material. Also depicted in FIG. 11H is a graft connection portion (76), in this variation taking the form of a small eyelet formed in the material of the radial extensions (64) which is configured to facilitate suturing between the radial extension (64) and a graft end (not shown).

Figure 12:
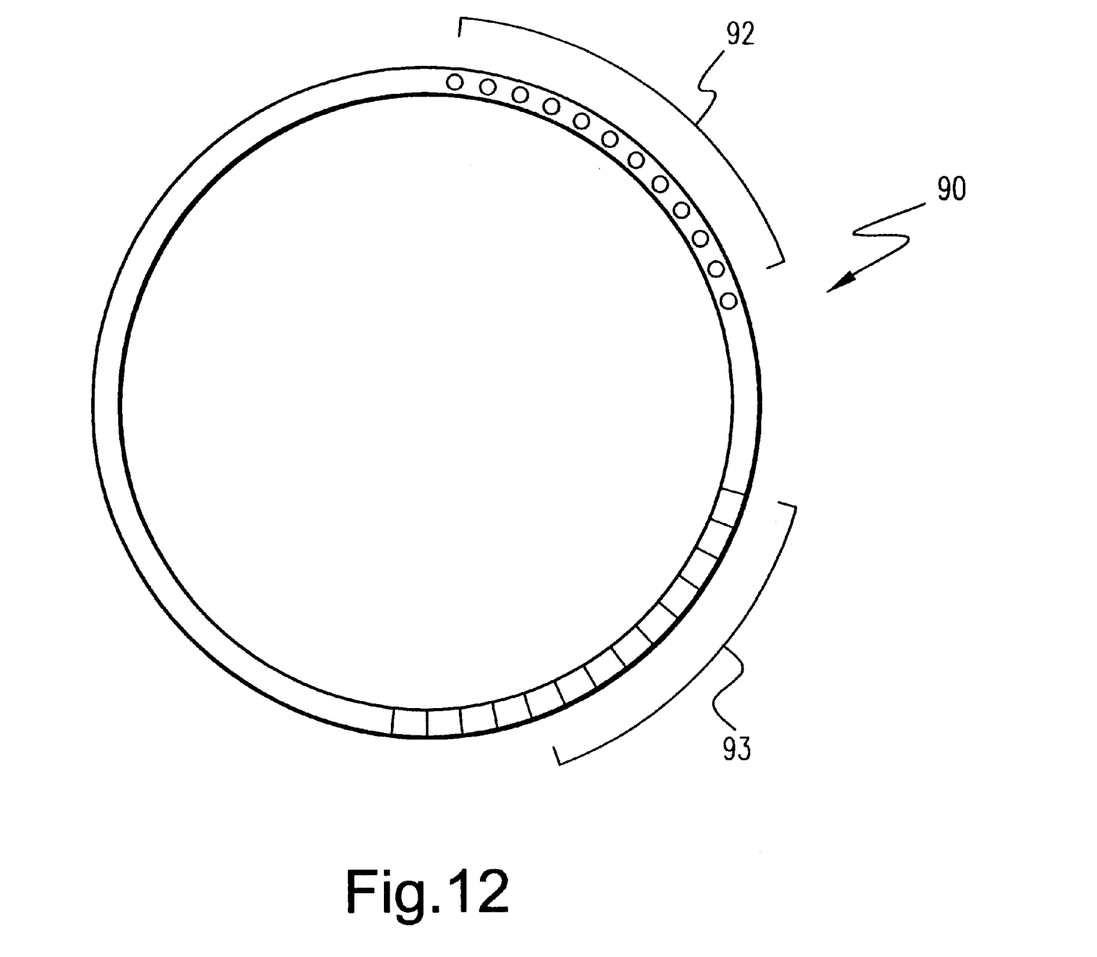
FIG. 12 depicts a top view of an external retention saddle for use with a live-lumen variation of the inventive device.

Referring to FIG. 12, an external retention saddle (90) is depicted in top view. The external retention saddle (90) is designed to interface with the tissue wall and distribute compressive loads to the tissues forming the tissue wall which result during and after installation of the device. The external retention saddle (90) is termed a "saddle" because of the shape it is capable for forming around the circumference of a hole in the side of a roughly cylindrical vessel. The external retention saddle (90) has a multitude of apertures (92) which are configured to interface with sew posts (not shown) which are configured to protrude through the tissue wall from the other side of the tissue wall. The apertures (92) of the external retention saddle may vary in geometry, depending upon the shape of the interfacing sew posts. The depicted embodiment has some roughly circular apertures (92) and some roughly rectangular apertures (93). The external retention saddle (90) is preferably comprised of a flexible biocompatible material, such as polyethylene or polyurethane, which may be precisely formed and is flexible enough to deform to saddle-like geometric configurations while being tough enough to distribute loads without fracturing.

Referring to FIGS. 13A–13F, a method for installing a live-lumen variation of the inventive device is depicted.

Figure 13A:
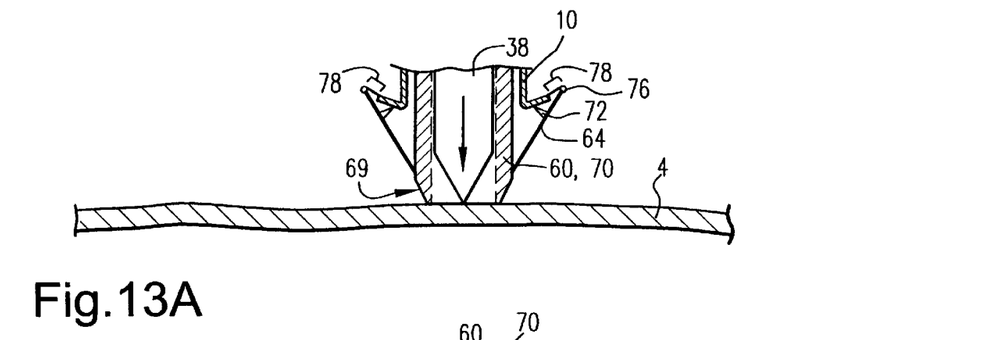
FIGS. 13A–13F depict a method for installing a live-lumen variation of the inventive device.

FIG. 13A shows a insertion structure (60) with a main shaft (70) having tapered ends (69) interfaced with a tissue wall (4) and slidably engaged with a trocar (38). Radial extensions (64) with sew posts (72) extending therefrom are shown in an unloaded position, coupled (76) with a live tissue graft member (10) by a suture (78). To facilitate insertion through a relatively-small aperture, the tapered ends (69) of the insertion structure (60) main shaft (70) have tapers which roughly match those of the trocar (38), as shown in the figure.

Figure 13B:
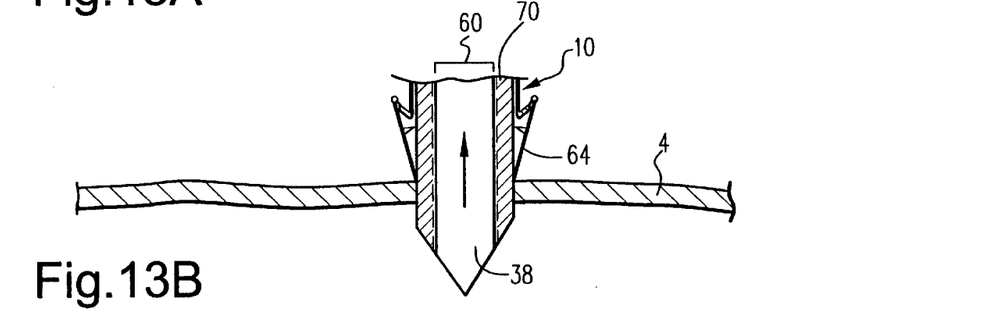
Figure 13C:
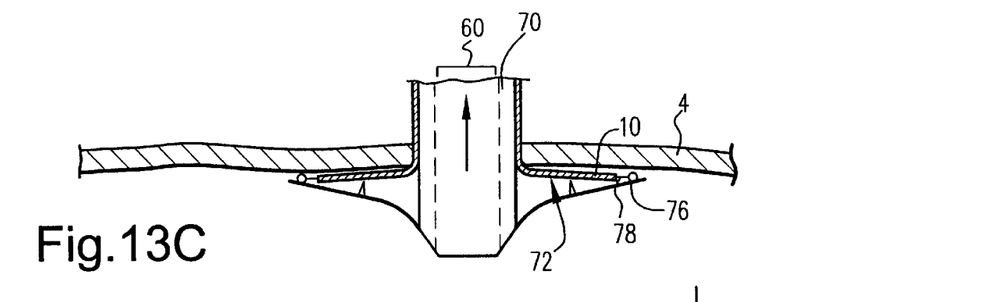

Referring to FIG. 13B, the trocar (38) and insertion structure (60) are urged through the tissue wall (4), causing the radial extensions (64) to be bent upward toward the main shaft (70) of the insertion structure (60). The trocar (38) is then removed and the insertion structure (60) pulled upwards, as is shown in FIG. 13C. FIG. 13C also shows that the graft member (10) is stretched outward as the insertion structure (60) is pulled upward, because the radial extensions (64), coupled (76) to the graft member by a suture (78), bend outwardly as they are urged toward the tissue wall (4).

Figure 13D:
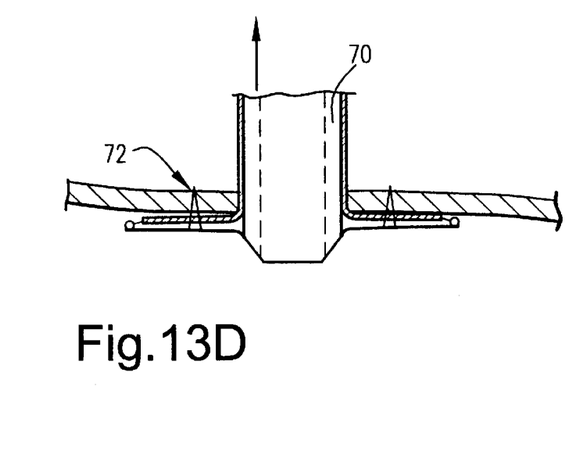
Figure 13E:
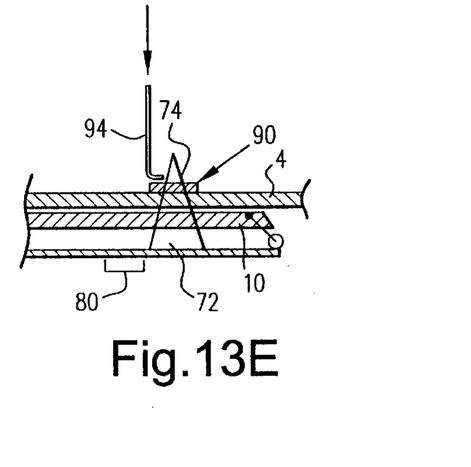

Referring to FIG. 13D, the insertion structure (60) is pulled upwards until the sharp-tipped sew posts (72) have been urged through both the graft member (10) and the tissue wall (4). The figure also depicts the location of the radial extension dislocation regions (80) of the radial extensions (64). FIG. 13E depicts the use of a blunt-end tool (94) to apply localized compression to the graft member (10) and tissue wall (4) by pressing down on a portion of a hand-placed external retention saddle as the insertion structure (60) is pulled upwards. This localized compression exposes a greater portion of the protruding sew post (72) and enables a suture to be passed through an aperture (74) in the sew post which will result in the proper compressive load upon the graft member (10) and tissue wall (4) which can be better distributed by the increased surface area of the external retention saddle (90).

Figures 13F, 14A:
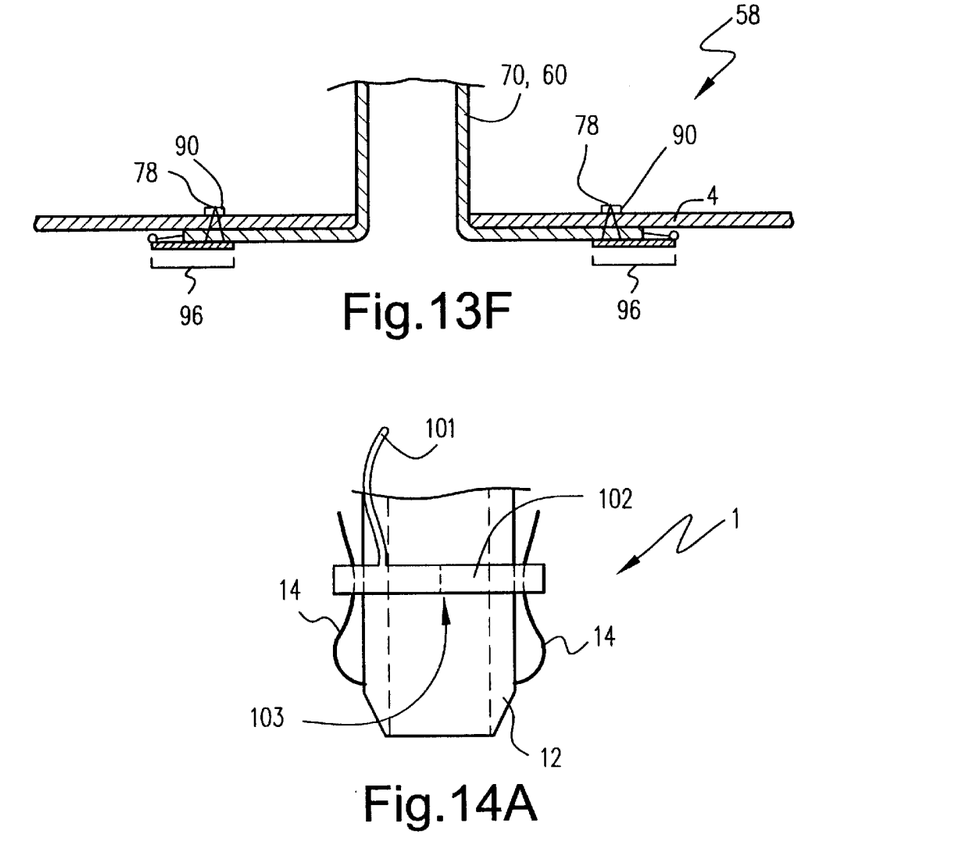
FIGS. 14A and 14B depict side views of two variations of the inventive device having restraining members coupled thereto.

As shown in FIG. 13F, after the external retention saddle has been completely installed via sutures (78) through sew post (72) apertures (74) circumferentially located about the anastomosis site, the upward load upon the the insertion structure (60) main shaft (70) can be removed and the insertion structure (60) released at the dislocation regions (80) of the radial extensions (64), leaving only small implanted portions (96) of the radial extensions, the external retention saddle (90) and related suture, and the intact live-tissue anastomosis junction, as is shown in FIG. 13F.

Figure 14B:
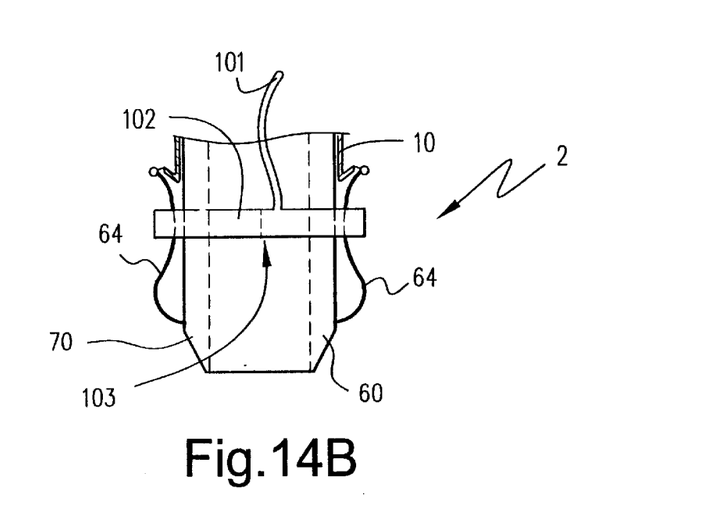

Referring to FIGS. 14A and 14B, synthetic-lumen (1) and live-lumen (2) variations, respectively, of the inventive anastomosis device are depicted with radial extensions (14, 64) restrained in an upward configuration by a restraining member (102), the restraining member (102) having a tension portion (101) configured to tear through a perforated zone (103) of the restraining member (102) upon application of a threshold tensile load, thus allowing the restraining member (102) to be pulled upward and away, and allowing the radial extensions (14, 64) to freely extend downward to their unloaded state, as depicted in FIGS. 3A and 11A.

The synthetic lumen variation of the inventive device may also be implanted in conjunction with a stent-like structural member, such as an implantable flow device having a side port or T-graft, for example, as described in the U.S. patent application for "Implantable Flow Diversion Device", attorney docket number 3659-5, incorporated by reference herein.

Each of the U.S. patent documents, U.S. patent application documents, foreign patent documents, and scientific reference documents (including texts and scientific journal articles) referred to in the text of this document is incorporated by reference into this document in its entirety.

Many alterations and modifications may be made by those of ordinary skill in the art without departing from the spirit and scope of this invention. The illustrated embodiments have been shown only for purposes of clarity. These examples should not be taken as limiting the invention defined by the following claims, said claims including all equivalents now or later devised.

What is claimed is:

1. An anastomosis device for joining the end of a tubular graft having a graft lumen with a tissue wall having an interior side and an exterior side comprising:

a. an implantable structural member having proximal and distal structural member ends, a longitudinal axis, an outer structural member surface, a structural member inner lumen, and at least two radial extensions extending outward from said structural member surface at the distal structural member end; and b. an implantable fastener having proximal and distal fastener ends and an inner fastener surface configured to slidably interface with said outer structural member surface, wherein said proximal end of said implantable structural member is configured to attach to said end of said tubular graft and fluidly connect said structural member lumen with said graft lumen, wherein said at least two radial extensions are configured to bend toward the outer structural member surface when said implantable structural member is urged, distal structural member end first, through an aperture in said tissue wall and to bend away from said outer structural member surface to prevent said implantable structural member from being removed from said aperture when said implantable structural member is urged in a reverse direction, and wherein said implantable fastener is operable to be moved distally along said outer structural member surface to reach a sustainable position wherein said tissue wall and said end of said tubular graft are retained in compression against each other between said implantable fastener and said at least two radial extensions.

2. The anastomosis device of claim 1 wherein said inner fastener surface and said outer structural member surface have threads, said threads causing said implantable fastener to move along the longitudinal axis of said implantable structural member as said implantable fastener is rotated in relation to said implantable structural member.

3. The anastomosis device of claim 1 wherein said inner fastener surface and said outer structural member surface have groove-locking undulatory interference geometries which allow said implantable fastener to move along the longitudinal axis of said implantable structural member after a threshold force is applied along said longitudinal axis.

4. The anastomosis device of claim 1 wherein the proximal end of said outer structural member surface comprises a compliant sew ring, said compliant sew ring configured to enable a sutured coupling between said end of said tubular graft and said proximal end of said implantable structural member.

5. The anastomosis device of claim 1 wherein said proximal structural member end has a porous region, said porous region having a multitude of small apertures configured to allow limited fluid contact between said structural member inner lumen and said outer structural member surface.

6. The anastomosis device of claim 1 further comprising a compliant load ring having a proximal surface, a distal surface, and an inner lumen, said compliant load ring being configured to prevent compressive stress concentrations between said implantable fastener and said at least two extensions.

7. The anastomosis device of claim 1 further comprising a slidable elongate trocar member having a proximal end and a distal wall-piercing end, said slidable elongate trocar member being slidably interfaced with the structural member inner lumen and configured to create a hole in said tissue wall through which the distal end of the implantable structural member may be urged.

8. The anastomosis device of claim 1 wherein the at least two radial extensions have tissue side and lumen side surfaces, the tissue side surfaces having extension pins designed to grasp the interior side of said tissue wall when said tissue side surfaces are urged against said tissue wall.

9. The anastomosis device of claim 1 wherein said implantable structural member comprises an oxygen sensor, said oxygen sensor being configured to monitor the oxygen content of fluids passing through said structural member inner lumen.

10. The anastomosis device of claim 9 wherein said oxygen sensor comprises a light source and a light sensor.

11. The anastomosis device of claim 1 wherein said implantable structural member comprises a fluid flow sensor, said fluid flow sensor being configured to monitor the flow of fluids through said structural member inner lumen.

12. The anastomosis device of claim 11 wherein said fluid flow sensor comprises a Doppler transducer.

13. The anastomosis device of claim 1 further comprising a radial extension restraining member, said radial extension restraining member being substantially tubular in shape and removably coupled about said implantable structural member in a delivery configuration wherein said at least two radial extensions are urged against said structural member surface, said at least two radial extensions being free to extend outward after said radial extension restraining member has been pulled toward said proximal structural member end and thereby uncoupled.

14. A method of using the anastomosis device of claim 1 comprising the steps of delivering said implantable flow diversion device to a desired location against said tissue wall, creating an aperture in said tissue wall at the location of said side hole, passing said distal structural member end through said tissue hole and said side hole, and placing said tissue wall and said implantable flow diversion device in compression between said implantable fastener and said at least two extensions.

15. An anastomosis device for joining a tubular graft with a tissue wall having an interior side and an exterior side comprising:

a. an insertion structure having a main shaft with proximal and distal ends, and at least two radial extensions, said at least two radial extensions comprising proximal and distal portions, the proximal portions being coupled to the distal end of said tubular graft, the distal portions being coupled to the tubular graft and releasably coupled to the proximal portions;

b. a threadlike wall attachment member;

wherein said at least two radial extensions are configured to bend toward said main shaft when a deployment construct, comprising said insertion structure with said main shaft partially encapsulated by said tubular graft and said tubular graft coupled to said distal portions, is urged, main shaft distal end first, through an aperture in said tissue wall from said external to said interior side, and to bend away from said main shaft to prevent said deployment construct from being removed from said small diameter hole when main shaft is urged in a reverse direction, and wherein said threadlike wall attachment member is attachable to said at least two radial extensions in a configuration operable to urge said radial extensions toward said lumen side of said tissue wall, thus placing said tissue wall and said tubular graft in compression against each other.

16. The anastomosis device of claim 15 wherein said threadlike wall attachment member comprises a suture placed through said tissue wall and around said at least two radial extensions.

17. The anastomosis device of claim 15 wherein each of said at least two radial extensions further comprises a piercing projection extending therefrom and being configured to pierce through said tubular graft and said tissue wall and provide an eyelet to which said threadlike wall attachment member may be coupled.

18. The anastomosis device of claim 15 wherein said at least two radial extensions are coupled to said tubular graft using a suture.

19. The anastomosis device of claim 17 further comprising an external retention saddle configured to be releasably attached to said tissue wall and said piercing projections by said threadlike wall attachment member, said external retention component operating to dissipate stress concentrations between said threadlike wall attachment member and said tissue wall.

20. The anastomosis device of claim 19, wherein said external retention saddle comprises a ringlike structure having a multitude of apertures through which said piercing projections may be placed.

* * * * *